United States Patent [19]

Larm et al.

[11] Patent Number: 4,707,471
[45] Date of Patent: Nov. 17, 1987

[54] WATER-SOLUBLE AMINATED β-1,3-BOUND D-GLUCAN AND COMPOSITION CONTAINING SAME

[75] Inventors: Olle Larm, Stockholm, Sweden; Rolf Seljelid, Tromsö, Norway

[73] Assignee: Medicarb AB, Stockholm, Sweden

[21] Appl. No.: 680,509

[22] Filed: Dec. 11, 1984

[30] Foreign Application Priority Data

Dec. 19, 1983 [SE] Sweden .............................. 8307026

[51] Int. Cl.$^4$ .................. C07H 15/04; C08B 37/00; A61K 31/70; A61K 31/73
[52] U.S. Cl. ........................................ 514/54; 514/56; 536/1.1; 536/17.2; 536/18.7; 536/21; 536/114; 536/123
[58] Field of Search .............. 536/1.1, 17.2, 123, 536/114, 18.7, 21; 514/54, 56

[56] References Cited

U.S. PATENT DOCUMENTS

| | | | |
|---|---|---|---|
| 3,822,250 | 7/1974 | Kimura et al. | 536/1.1 |
| 3,856,775 | 12/1974 | Fukuoka et al. | 536/1.1 |
| 4,075,405 | 2/1978 | Takahashi et al. | 536/114 |
| 4,143,201 | 3/1979 | Miyashiro et al. | 536/1.1 |
| 4,396,611 | 8/1983 | Duc | 514/54 |

FOREIGN PATENT DOCUMENTS 0083798 6/1980 Japan ............................ 514/54

Primary Examiner—Ronald W. Griffin
Attorney, Agent, or Firm—Burns, Doane, Swecker & Mathis

[57] ABSTRACT

Water-soluble aminated β-1,3-bound D-glucan and macrophage-stimulating composition containing as an active constituent such glucan.

19 Claims, 7 Drawing Figures

WATER-SOLUBLE AMINATED β-1,3-BOUND D-GLUCAN AND COMPOSITION CONTAINING SAME

The present invention relates to water-soluble aminated β-1,3-bound D-glucans and a composition containing as an active constituent one or several such glucans in combination with a pharmaceutically acceptable carrier. The glucans according to the invention possess ability to activate mononuclear phagocytes, so called macrophages.

It is known that certain polysaccharides improve the defense mechanism of the body, i.a. by activating the complement system and stimulating the function of monocytes-macrophages. These cells are of a central importance to the defense of the body both from inside and outside, for example against the growth of cancer cells, and attack from, for example bacteria, respectively. It has been previously shown (GLYCAN STIMULATION OF MACROPHAGES IN VITRO, R. Seljelid, G. Bogwald and A. Lundwall, Experimental Cell Research 131 (1981) 121), that certain and necessarily nonsoluble glucans, particularly such glucans containing 1,3-bound β-D-glucose entities, activate macrophages in vitro making same cytotoxic. Since insoluble compounds are unsuitable to use both in vitro and in vivo the invention has for its major object to provide soluble derivatives of β-1,3-D-glucans for the purpose of obtaining soluble compounds of maintained capacity to activate macrophages.

The expression "macrophage" as used in this context refers to mononuclear phagocytes which is a scientifically more adequate expression.

In accordance with the present invention it has been found that by substituting soluble β-1,3-bound D-glucans with aminogroups or with compounds containing aminogroups it is possible to prepare soluble compounds of a carbohydrate nature which have the ability of stimulating mononuclear phagocytes, i.e. macrophages. Compounds which in this manner stimulate the macrophages are often found to be both cytostatic and cytotoxic against a certain type of cancer cells, for example L 929 in vitro.

Comprehensive studies and experiments have shown that aminated soluble glucans containing β-1,3-bound D-glucose-entities have the ability of activating macrophages. The activity of the modified polysaccharides is depending on the number of aminogroups introduced. The importance of the presence of aminogroups in such aminated, soluble glucans has been shown by acetylation of the aminogroups which results in a decrease in activity.

In connection with the birth of the invention and experiments carried out it has been established that neither the macrographs as such, nor macrophages in the presence of aminated glucans exert any growth-inhibiting effect on normal embryonic fibroblast cells. This observation confirms early reports about the fact that there is a certain degree of specificity of the cytotoxic and cytostatic effect of the macrophages (cf. MACROPHAGE NON-IMMUNOGENIC RECOGNITION: TARGET CELL FACTORS RELATED TO CONTACT INHIBITION Y. B. Hibbs, *Science* 180 (1972) 868). The observation furthermore indicates that aminated glucans under certain clinical conditions can be considered as potential pharmaceutics having a high degree of specificity as regards the killing of cancer cells. It is not clear why soluble aminated β-1,3-bound D-glucans make macrophages cytotoxic while hydrolyzed, soluble glucans lack effect. Even if the invention is not to be considered to be limited to any specific theory it is possible that the aminofunctions provide for binding of the polysaccharide to negatively charged groups on the surfaces of the tumor cell, thereby presenting same as an insoluble particle to the macrophage.

In accordance with the present invention there are thus provided water-soluble aminated β-1,3-bound D-glucans. The glucans are preferably selected from the group consisting of laminaran, curdlan, pachyman, yeast glucan and lichenan. Particularly preferred glucans are aminated curdlans and laminaran.

As previously indicated the glucans according to the present invention have the ability of activating mononuclear phagocytes, i.e. macrophages, and are therefore useful to inhibit the growth of cancer cells.

The glucans according to the present invention are preferably aminated to a nitrogen content of at least about 1%, and the aminogroups present are suitably mainly primary ones.

The invention also provides for a macrophage-stimulating composition containing as an active constituent a glucan according to the invention in combination with a pharmaceutically acceptable carrier.

The active aminated glucans according to the present invention may, in a conventional manner, be formulated for use in human or veterinary medicine. The composition of the pharmaceutical preparation may contain the active constituants in combination with a pharmaceutically acceptable carrier, which may be solid, semi-solid or liquid depending on the manner of administration and other circumstances. The active constituents may also be used as such without additional carrier materials. The compositions are prepared in exact concordance with conventional pharmaceutical practice.

As previously indicated the function of the mononuclear phagocytes is of essential importance to the defense of the body both when influenced internally and externally. The present invention provides for substances which have the ability of generally activating the defense system of the body, for example against the growth of cancer cells, infections etc. Such applications are of interest to vertebral animals of different kinds, covering animals including man, fishes etc. In order to reduce the tendency for the creation of diseases in for example fishes cultivated under controlled conditions the glucans according to the present invention may advantageously be supplied to the environment of the fishes, either directly into the water where cultivation takes place or as a food additive. The invention is particularly useful in connection with the cultivation of high-quality fish, such as salmon, trout or similar species.

The invention will in the following be further illustrated by specific examples. The description is made in connection to the appended drawings, wherein FIG. 1 shows a diagram on introduction of radioactive tymidine in cultures of L 929 cells Incorporation of radioactive thymidine in cultures of L 929 cells with the following additives: △ no additive; ▲ aminated glucan ($P_1$); o normal macrophages; • normal macrophages+aminated glucan ($P_1$). The results are given as percentage of maximal incorporation in L 929 cells without any additives (14,000 cpm/well for 72 to 96 hours), mean value+standard deviation.

FIG. 2 shows a diagram on dose response using aminated curdlan;

Dose-response with aminated curdlan ($P_1$) concerning cytostatic effect in L 929 cells. ● L 929 with aminated curdlan ($P_1$); ○ L 929 cells with aminated curdlan ($P_1$) and macrophages. The results are given as mean values±standard deviation.

FIG. 3 shows a diagram on the introduction of radioactive tymidine in cultures of embryonic fibroblasts;

Incorporation of radioactive thymidine in cultures of embryonic fibroblasts from 48 to 96 hours in vitro. The results are given as percentage of incorporation in embryonic cultures without any additives, mean value±standard deviation.

(1) Non-stimulated macrophages and embryonic cells.
(2) Macrophages stimulated by aminated glucan (20 ug/ml) and embryonic cells.
(4) Embryonic cells and aminated glucan (20 ug/ml).

FIG. 4 shows a diagram on specific lysis of L 929 cells;

Specific lysis of L 929 cells in co-culture with macrophages during 5 days with the following additives:

(1) No additive.
(2) Hydrolyzed, water-soluble β-1,3-D-glucan (20 ug/well).
(3) Aminated, soluble β-1,3-D-glucan (20 ug/well).
(4) Insoluble, native β-1,3-D-glucan (40 ug/well).

The results are given as mean values±standard deviation.

Figure 1:
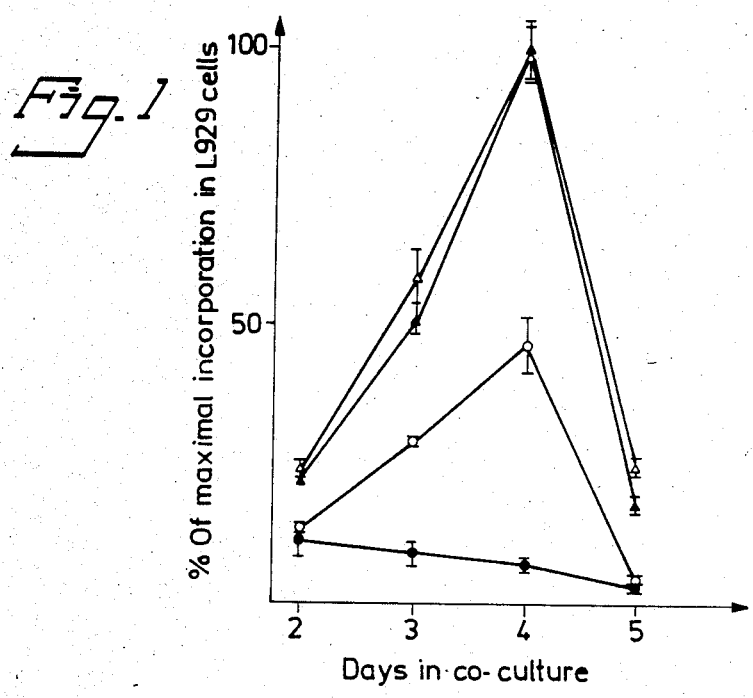
Figure 2:
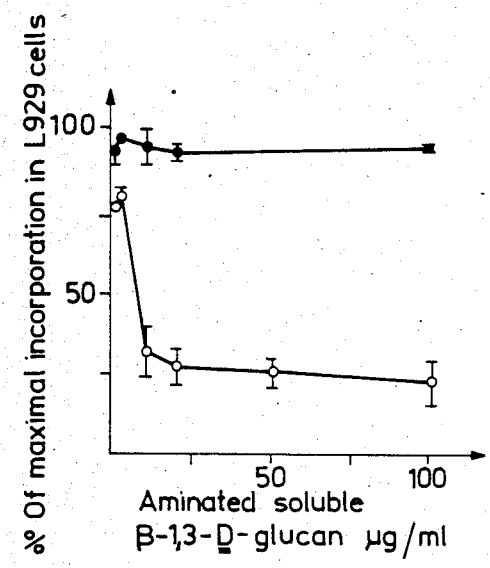
Figure 3:
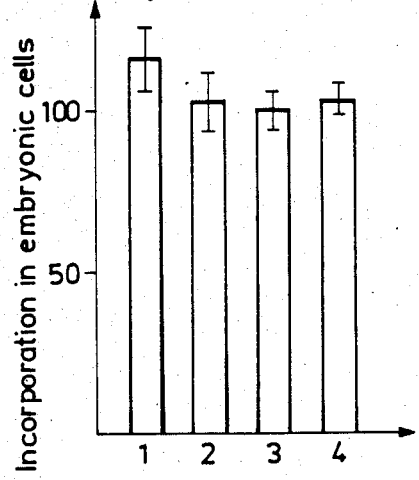
Figure 4:
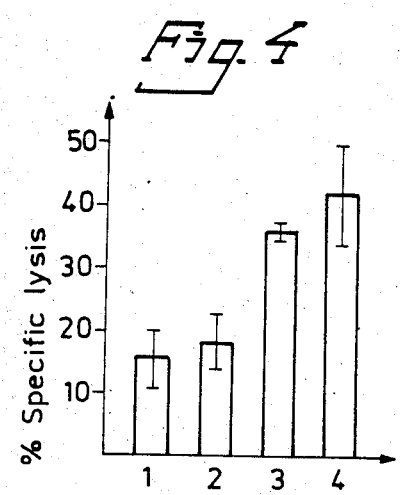
Figure 5:
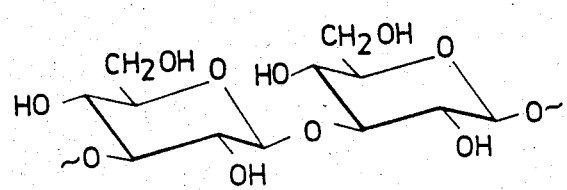
FIG. 5 shows the basic building stone in the glucans which are starting materials in the amination.

For the sake of good order FIG. 5 shows the critical structure element in glucans used as starting materials for amination to form the water-soluble aminated glucans according to the present invention.

BIOLOGICAL PROCEDURE

Macrophage cultures

Macrophages were obtained from hybrid $C_3D_2$ (C3H/Tif×DBA/2) mice made available by Gl. Bomholtgard, Ltd., Ry, Denmark. Peritoneal cells ($0.7 \times 10^6$ cells) were transferred on to glass cover slips (diameter 14 mm) in circular wells in Costar tissue culture plates (Costar, Cambridge, Mass., USA). After two hours in culture, nonadherent cells at the bottom of the well were washed away. The cells were held in culture in Eagle's medium (DME) modified by Dulbecco with 10% heat inactivated (56° C., 30 min.) serum from newborn calves ("newborn calf serum", NDBC, Gibco Biocult Ltd., Paisley, Scotland). All media contained penicillin (100 IE/ml) and streptomycin (100 µg/ml). The cells were cultured at 37° C. in a humidified atmosphere containing 5% $CO_2$. Analysis using fluorescence microscopy showed that there were less than 1% lymphocytes in the cultures.

Target cells

The fibroblast cell line L 929 (3) transformed in vitro was cultured in DME using 10% heat inactivated NBCS. Embryonic fibroblast cultures were obtained by mixing 14 days old Balb/cembryos in DME with 10% heat inactivated NBCS and transferring the whole suspension to tissue culture plates. After two days cells and non-adhering tissue fragments were washed away and the remaining cells were allowed to grow. These cells were morphologically of the fibroblast type.

Measuring macrophage-mediated cytostasis

Target cells ($2 \times 10^4$ cells/well) were treated with trypsine and were added to macrophage cultures 24 hours after stimulation with aminated glucan. After different time intervalls 0.5 µCi/ml radioactive thymidine (methyl-$^3$H, New England Nuclear, Dreieich, West Germany) were added to the cultures. The incorporation was measured after an incubation period of 24 hours. After harvesting the cultures the highmolecular material was precipitated with 1M perchloric acid and thoroughly washed before dissolution in 1M sodium hydroxide solution. The dissolved material was transferred to measuring cells and analyzed in a scintillation counter (Packard Instruments International, Zürich, Switzerland).

Method for measuring macrophage-mediated cytotoxicity

Target cells were labelled for 24 hours with radioactive thymidine (methyl-$^3$H, 0.5 µCi/ml). Before addition to macrophage cultures the target cells were thoroughly washed to remove non-incorporated radioactively labelled thymidine. Release of radioactively labelled substance was measured every day in 50 µl aliquotes carefully drawn from the culture medium. The total amount of incorporated radioactivity was determined in ultrasound-treated samples of the target cells. The radioactive samples were analyzed in a scintillation counter. Macrophage-mediated cytolysis of target cells was expressed as percentage specific lysis:

$$\frac{\text{(target-cells + macrophages) − medium cpm (target-cells)}}{\text{total incorporated cpm of target-cells}} \times 100$$

Method for measuring stimulation of macrophages $^{14}$C-labelled D-glucoseamine and the aminated soluble β-1,3-bound D-glucan are added to macrophage cultures. Increased incorporation of D-glucoseamine in glycoproteins of macrophages is an activation parameter for macrophages. 24 hours after the addition of the carbohydrates the cells are dissolved in 5% trichloro acetic acid and non-incorporated radioactive D-glucoseamine is washed away. The washed cells are dissolved in sodium hydroxide (1M). After dissolution of all cell material the solution is transferred to measuring cuvettes and the radioactivity is measured in a scintillation counter. The degree of activation is expressed by the quotient:

$$\text{stimulation} = \frac{\text{cpm }^{14}\text{C glucoseamine polysaccharide-stimulated macrophages}}{\text{cpm }^{14}\text{C glucoseamine-stimulated macrophages}}$$

CHEMICAL PROCEDURE, EXAMPLES

Example 1

Preparation of hydrolyzed, soluble β-1,3-bound D-glucan

Curdlan and laminaran (1 g), β-1,3-bound D-glucans, were hydrolyzed with 90% formic acid (25 ml) at 95° C. for 20 minutes. The acid was removed by evaporation at low pressure, water was added (50 ml) and the reaction mixture was refluxed for 1 hour. After evaporation to a smaller volume the reaction mixture was separated on a Sephadex G-50 column and the material of highest molecular weight (~100 mg) was recovered and used for further reactions.

Example 2, amination

Curdlan (100 mg) hydrolyzed as per Example 1 was dissolved in water 4 ml and a solution of bromine ($Br_2$) in water (12 ml, 0.1M) was added. The pH value was adjusted to 7.0 and was kept constant at this value by addition of sodium hydroxide (NaOH, 0.1M). The reaction mixture was allowed to stand under stirring in room temperature until all bromine had been consumed(24-48 hours). The pH value was adjusted to 5.0 and the reaction mixture was dialyzed against distilled water and freeze dried (yield 90 mg). A solution of ammonium acetate (2 g) in water (1 ml) was adjusted to 7.0 with acetic acid. Curdlan (90 mg) oxidized with bromine according to the above was added together with sodium cyanoborohydride (120 mg) and the reaction mixture was allowed to stand with stirring for 7 days. The pH value was adjusted to 4.0 with acetic acid and the solution was allowed to stand for further three hours at room temperature. After dialyzis against distilled water and freeze drying 80 mg of aminated curdlan could be isolated. The product was analyzed with elementary analysis and $^{13}$C-n.m.r.

Figure 6:
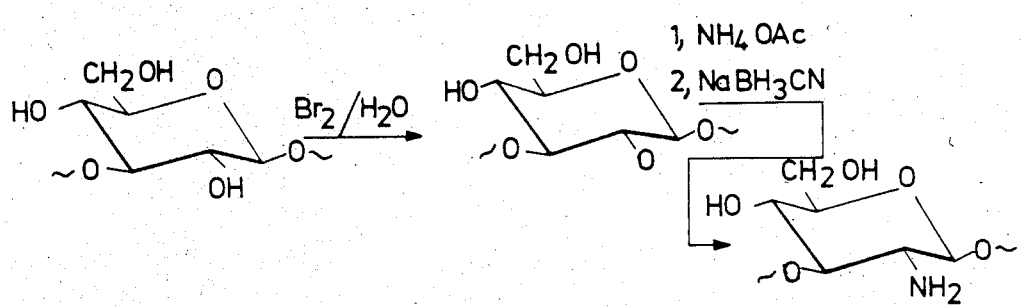
FIG. 6 illustrates a conceivable amination reaction.

The synthesis method described in this example is illustrated with structural formulae in FIG. 6.

Example 3

The amination was performed as per Example 2 but with the modification that 1 g 1,6-diaminohexane was used instead of ammonium acetate.

Example 4

Laminaran (100 mg) hydrolyzed as per Example 1 was dissolved in dimethylsulfoxide (DMSO, 4 ml) in a serum bottle under nitrogen gas, and sodium-tert-butoxide (1 ml, 3M in DMSO) was added with an injection syringe. The mixture was allowed to stand in an ultrasonic bath for half an hour and then at room temperature over night. In dependence on the desired degree of substitution different quantities of chloracetaldehyde dimethylacetal were then added. The reaction mixture was separated on a Sephacryl S-400 column using water as an eluant. After freezedrying the substitution yield for alkylation according to different conditions was calculated using $^1$H-n.m.r. The integral for the signal of OMe-groups in the acetal were compared to the integral of the anomeric protone (H-1) in the polysaccharide. By varying the quantity of chloroacetaldehyde dimethylacetal, polysaccharides were obtained having from 0.03 to 0.39 acetal groups per glucose entity (yield ~75%).

The acetal groups of the alcylated polysaccharides were removed by acid hydrolysis (0.025M hydrochloric acid, 100° C. and 15 minutes). The reaction mixtures were neutralized (NaOH, 1M), dialyzed and freeze-dried (yield 80%).

Figure 7:
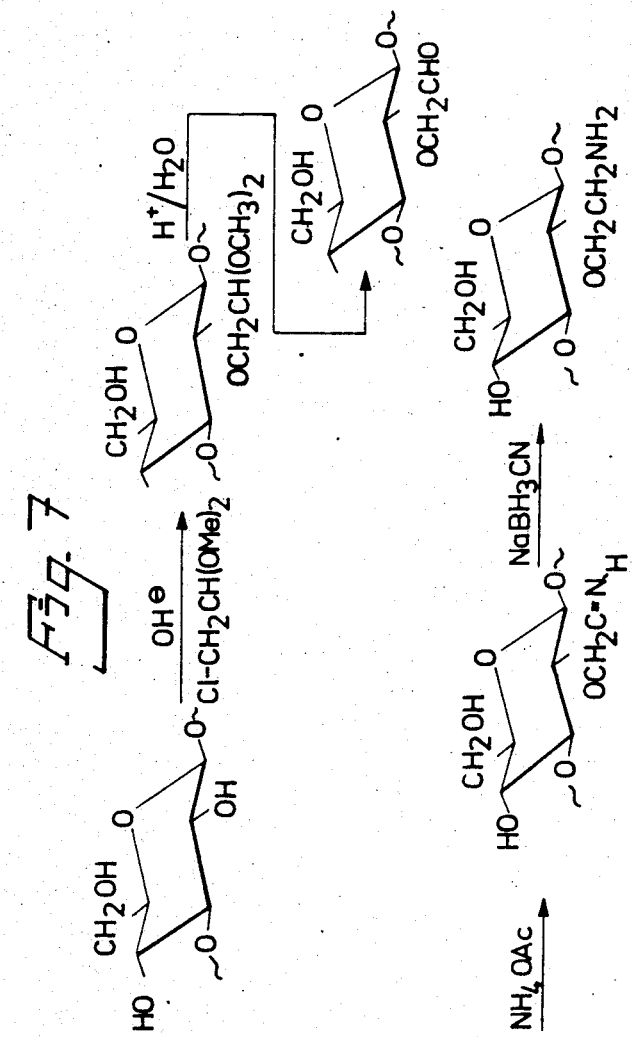
FIG. 7 illustrates an alternative amination procedure.

Aminations were carried out with ammonium acetate in 1,6diaminohexane as in Examples 2 and 3. The amination sequence is diagramatically illustrated in FIG. 7.

The test results are presented in Table 1 below. In this table the polysaccharides $P_1$ and $P_2$ were prepared in accordance with Example 2, $P_5$ and $P_6$ according to Example 3 and $P_3$, $P_4$ and $P_7$ according to Example 4. Polysaccharide $P_8$ corresponds to polysaccharide $P_1$ acetylated on the nitrogen using acetic anhydride in pyridine.

TABLE 1
STIMULATION USING AMINATED β-1,3-BOUND D-GLUCANS

| Polysaccharide | Substituent | % N | COOH | Stimulation |
|---|---|---|---|---|
| $P_1$ | $-NH_2$ | 1.2 | + | 2.1 |
| $P_2$ | $-NH_2$ | 0.6 | + | 1.0 |
| $P_3$ | $-OCHCH_2NH_2$ | 1.8 | − | 3.9 |
| $P_4$ | $-OCH_2CH_2NH_2$ | 1.4 | + | 2.5 |
| $P_5$ | $-NH(CH_2)_6NH_2$ | 1.3 | + | 1.2 |
| $P_6$ | $-NH(CH_2)_6NH_2$ | 0.66 | + | 1.0 |
| $P_7$ | $-OCH_2CH_2NH(CH_2)_6NH_2$ | 2.5 | − | 12.8 |
| $P_8$ | $-NHCCH_3$ with =O | 1.2 | + | 1.6 |

We claim:

1. A water-soluble aminated β-1,3-bound D-glucan wherein the glucan is selected from the group consisting of laminaran, curdlan, pachyman, yeast glucan and lichenan.

2. The water-soluble aminated β-1,3-bound D-glucan according to claim 1 wherein the glucan is selected from the group consisting of curdlan and laminaran.

3. The water-soluble aminated β-1,3-bound D-glucan according to claim 1 wherein the glucan is curdlan and is substituted in the 2-position with an $-NH_2$ group.

4. The water-soluble aminated β-1,3-bound D-glucan according to claim 1 wherein the glucan is curdlan and is substituted in the 2-position with an $-OCH_2CH_2NH_2$ group.

5. The water-soluble aminated β-1,3-bound D-glucan wherein said aminated substituent is selected from the group consisting of $-NH_2$, $-OCHCH_2NH_2$, $-OCH_2CH_2NH_2$, $-NH(CH_2)_6NH_2$, $-OCH_2CH_2NH(CH_2)_6NH_2$ and $-NHCOCH_3$.

6. A macrophage-stimulating composition containing as an active constituent a water-soluble aminated β-1,3-bound D-glucan, wherein the glucan is selected from the group consisting of laminaran, curdlan, pachyman, yeast glucan and lichenan in combination with a pharmaceutically acceptable carrier.

7. A composition according to claim 6 wherein the glucan is selected from the consisting of curdlan and laminaran.

8. A composition according to claim 6 wherein the aminated glucan essentially contains primary amino groups.

9. A composition according to claim 8 wherein the glucan is curdlan and is substituted in the 2-position with an $-NH_2$ group.

10. A composition according to claim 8 wherein the glucan is curdlan and is substituted in the 2-position with an $-OCH_2CH_2NH_2$ group.

11. A macrophage-stimulating composition containing as an active substituent a water-soluble aminated β-1,3-bound D-glucan wherein the aminated substituent is selected from the group consisting of $-NH_2$, $-OCHCH_2NH_2$, $-OCH_2CH_2NH_2$, $-NH(CH_2)_6NH_2$, $-OCH_2CH_2NH(CH_2)_6NH_2$ and $-NHCOCH_3$ in combination with a pharmaceutically acceptable carrier.

12. A method for activating mononuclear phagocytes in vertebral animals comprising administering to an animal in need of such treatment a sufficient amount of a water-soluble aminated β-1,3-bound D-glucan to activate mononuclear phagocytes.

13. A method according to claim 12 wherein the glucan is selected from the group consisting of laminaran, curdlan, pachyman, yeast glucan and lichenan.

14. A method according to claim 13 wherein the glucan is selected from the group consisting of curdlan and laminaran.

15. A method according to claim 12 wherein the glucan is aminated to a nitrogen content of at least about 1%.

16. A method according to claim 12 wherein the aminated glucan essentially contains primary amino groups.

17. A method according to claim 16 wherein said glucan is curdlan and is substituted in the 2-position with an —NH$_2$ group.

18. A method according to claim 16 wherein said glucan is curdlan and is substituted in the 2-position with an —OCH$_2$CH$_2$NH$_2$ group.

19. A method for activating mononuclear phagocytes in vertebral animals comprising administering to an animal in need of such treatment a sufficient amount of a water-soluble aminated $\beta$-1,3-bound D-glucan to activate mononuclear phagocytes wherein the aminated substituent is selected from the group consisting of —NH$_2$, —OCHCH$_2$NH$_2$, —OCH$_2$CH$_2$NH$_2$, —NH(CH$_2$)$_6$NH$_2$, —OCH$_2$CH$_2$NH(CH$_2$)$_6$NH$_2$, and —NHCOCH$_3$.

* * * * *